United States Patent
Zamore

(10) Patent No.: US 6,558,732 B1
(45) Date of Patent: *May 6, 2003

(54) PROCESS FOR PRODUCING AN IMPLANTABLE APPARATUS COMPRISING A BIOMEDICAL DEVICE COATED WITH CROSSLINKED TPU

(76) Inventor: Alan M. Zamore, 600 D Rte. 45, Chestnut Ridge, NY (US) 10977

( * ) Notice: Subject to any disclaimer, the term of this patent is extended or adjusted under 35 U.S.C. 154(b) by 0 days.

This patent is subject to a terminal disclaimer.

(21) Appl. No.: 09/442,618

(22) Filed: Nov. 17, 1999

Related U.S. Application Data
(60) Provisional application No. 60/108,961, filed on Nov. 18, 1998.

(51) Int. Cl.⁷ .................. B05D 3/06; A61L 27/00
(52) U.S. Cl. ............... 427/2.24; 427/2.28; 427/2.25; 427/2.3; 427/2.31; 427/487; 427/496; 427/508; 427/551; 427/553; 427/558; 427/595; 427/596
(58) Field of Search ................ 427/2.24, 2.25, 427/2.28, 2.3, 2.31, 487, 496, 508, 551, 553, 558, 595, 596

(56) References Cited

U.S. PATENT DOCUMENTS

| | | | |
|---|---|---|---|
| 4,255,552 A | * | 3/1981 | Schollenberger et al. ...... 528/50 |
| 4,567,083 A | * | 1/1986 | Arioka et al. ............... 428/141 |
| 4,676,975 A | * | 6/1987 | McGary et al. ............. 424/423 |
| 4,762,884 A | * | 8/1988 | Goyert et al. ................. 525/28 |
| 4,786,657 A | * | 11/1988 | Hammar et al. .............. 522/90 |
| 5,094,876 A | * | 3/1992 | Goldberg et al. .............. 427/2 |
| 5,109,097 A | * | 4/1992 | Klun et al. .................... 528/75 |
| 5,433,744 A | * | 7/1995 | Breyen et al. .............. 607/125 |
| 5,461,133 A | * | 10/1995 | Hammar et al. .............. 528/10 |
| 5,670,097 A | * | 9/1997 | Duan et al. ................ 264/1.24 |
| 5,998,085 A | * | 12/1999 | Isberg et al. ................ 430/200 |

* cited by examiner

Primary Examiner—Shrive P. Beck
Assistant Examiner—Jennifer Kolb Michener
(74) Attorney, Agent, or Firm—Dale L. Carlson; Wiggin & Dana L.L.P.

(57) ABSTRACT

A method for producing increased resistance to biodegradability is provided for biomedical devices subject to in vivo implantation. Among the steps required to produce such resistance are the application of a thermoplastic polyurethane coating to the device to provide a coating, and the subsequent crosslinking of the thermoplastic polyurethane coating through the application of radiation of a sufficient intensity and duration to convert said thermoplastic polyurethane coating to a thermoset coating possessing the attribute of increased biostability.

12 Claims, 1 Drawing Sheet

PROCESS FOR PRODUCING AN IMPLANTABLE APPARATUS COMPRISING A BIOMEDICAL DEVICE COATED WITH CROSSLINKED TPU

CROSS REFERENCE TO RELATED APPLICATIONS

This patent application claims the priority benefit of U.S. Provisional Patent Application Ser. No. 60/108,961 filed on Nov. 18, 1998, incorporated by reference in its entirety herein.

BACKGROUND OF THE INVENTION

1. Field of the Invention

This invention relates to the use of crosslinked thermoplastic polyurethane elastomeric materials as a coating for biomedical devices, more particularly to the use of such materials as a coating surrounding implantable biomedical devices, and more specifically the electrical leads attached thereto.

2. Description of Related Art

The use of thermoplastic polyurethane (TPU) and other synthetic materials which resist biodegradability to coat the electrical leads of heart pacemakers and other implantable biomedical devices is well known. Typically, a heart pacemaker is implanted surgically into the body and wires are extended from the electrical pacing device to the heart muscle. Amongst synthetically produced materials, polyurethane possesses an attribute of relative biocompatibility. Simply stated, polyurethane resists both post-implantation tissue rejection, as well as the degradation caused by contact with animal tissues and fluids, to a greater extent than most other polymers, except arguably silicone rubber.

However, polyurethanes are not totally biocompatible and exhibit certain disadvantageous degradations which become evident over time. These degradations can include hydrolytic degradations wherein mechanical properties such as tensile strength, elongation and elasticity are affected. In fact, many polyurethanes will decompose completely from hydrolytic degradation as a result of prolonged implantation. Another form of degradation consists of environmental stress cracking. Environmental stress cracking results in the generation of crazes or cracks in the polyurethane elastomer which are themselves produced by the combined interaction of a medium capable of acting on the elastomer, in this case blood and other bodily fluids, and a stress level above a specific threshold. Yet another form of degradation is that of metal ion induced oxidation (MIO). MIO is distinguished by the accelerated degradation of polyurethane elastomers resulting from contact with metal ions used alone or as alloys in pacing lead conductors.

Regardless of the specific mechanism giving rise to the degradation, the end result is one of scission of the polyurethane chain with an attendant decrease in molecular weight and a loss of desireable properties, including that of biocompatibility. As a result, the functionality of the TPU coated pacemaker and especially the leads, over time may eventually fail thereby endangering the life of the patient. To avoid this possibility of failure the implanted pacemaker leads, are often preemptively surgically replaced on the order of every five to ten years. Any substantial increase in the lifetime of pacemaker leads would serve to minimize the unnecessary surgical trauma involved in pacemaker lead replacement. As mentioned, the use of thermoplastic TPU as insulation on pacemaker leads is known. In addition, attempts to develop polyurethanes and pacemaker leads with improved biocompatibility are disclosed in the patent literature. U.S. Pat. Nos. 4,875,308, 5,133,742, and 5,109,107 disclose the development of polyurethanes substantially free of ether linkages. U.S. Pat. No. 4,851,009 discloses the development of polyurethane pacemaker leads coextruded with ajacket covering of silicon rubber. Lastly, U.S. Pat. No. 5,419,921 discloses the development of polyurethane pacemaker leads jacketed with a thin layer of polycarbonate polyurethane. However, there is no teaching in these references suggesting a substantially positive effect on the long term biocompatibility of polyurethanes, in general, or of cardiac pacemakers in particular.

BRIEF SUMMARY OF THE INVENTION

Accordingly, it is a primary object of the invention to provide a method for making an coated electrically insulating flexible wire or lead for use with cardiac pacemakers, defibrillators, or other biomedical devices exhibiting improved biostability and biocompatibility following in vivo implantation.

In accordance with the invention, there is provided an apparatus comprised of a biomedical device coated with a flexible insulator applied and crosslinked by actinic radiation.

The process of crosslinking stabilizes polymers in general as described in more detail in U.S. Pat. No. 5,900,444, incorporated herein by reference in its entirety. In particular, crosslinking stabilizes thermoplastic polyurethanes while increasing their heat, solvent, and environmental stress crack resistance. The use of crosslinked thermoplastic polyurethanes in place of uncrosslinked TPU offers the promise of a greater lifetime for biomedical devices in general used in in-vivo implantation, and pacemaker wires in particular. Wires or leads, and even whole devices can be coated or jacketed with TPU, subsequently or simultaneously radiation crosslinked to a dose between 1 and 100 MRads, and then utilized for implantation purposes. It is expected that such crosslinking of TPU will afford additional protection against the degrading effects of long term exposure to animal tissues and fluids. Therefore, in accordance with the invention, biomedical devices and the electrical leads attached thereto can be coated with thermoplastic polyurethane, a blend of different thermoplastic polyurethanes, a blend of thermoplastic polyurethanes and other polymers, such as a silicone polymer, or with polyurethane copolymerized with other moities such as silane. In addition, all of these coating materials may be suitably combined with a crosslinking agent to facilitate crosslinking of the TPU is the presence of radiation. This coating, whether containing a crosslinking agent or not, is then suitably converted through the application of radiation to produce a thermoset polyurethane exhibiting the attributes of both biostability and biocompatibility.

DETAILED DESCRIPTION

Figure 1:
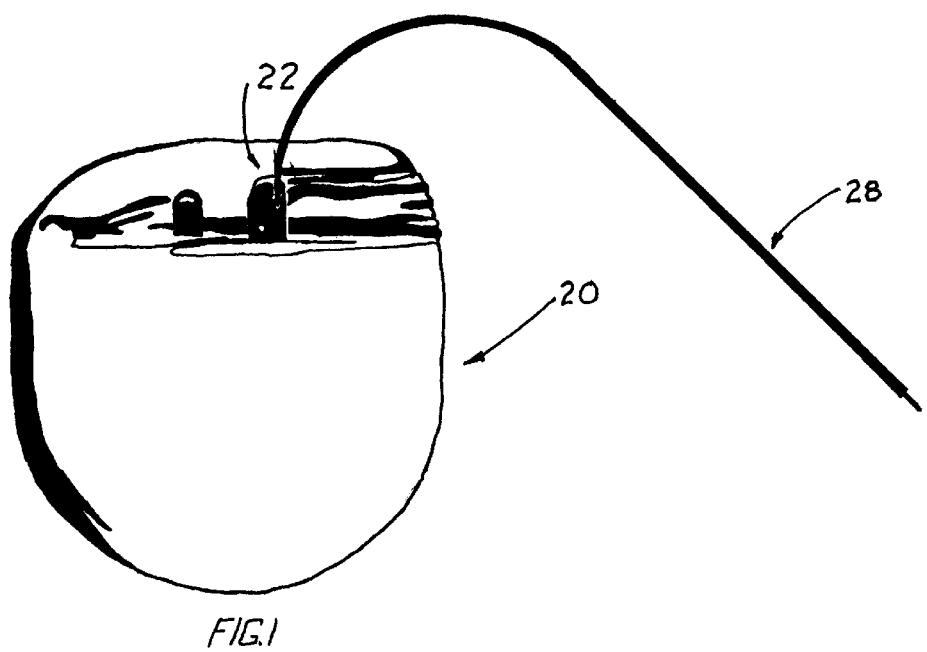
FIG. 1 is a rendering of a cardiac pacemaker illustrating the placement of the primary electrical lead.
Figure 2:
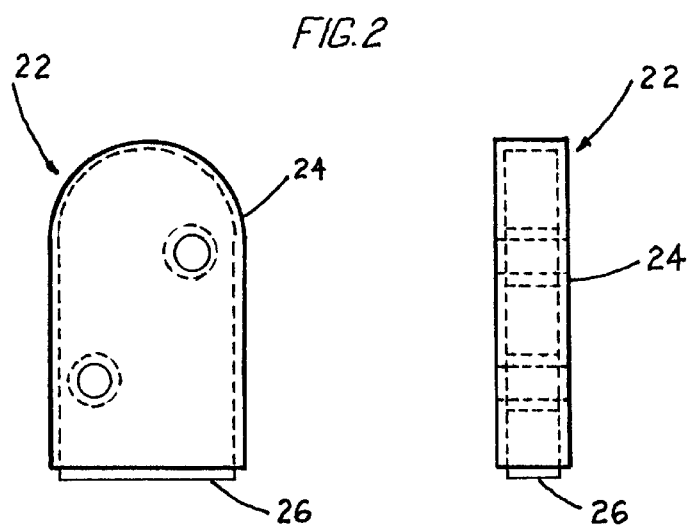
FIG. 2 is a schematic of a generic lead contact coated with crosslinked TPU.
Figure 3:
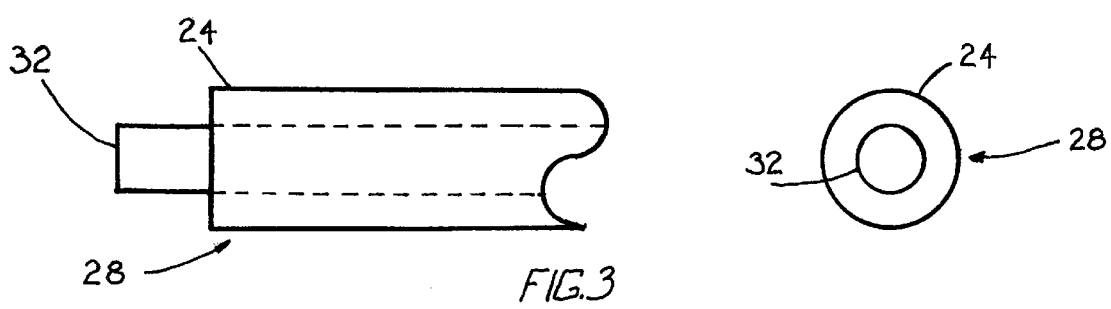
FIG. 3 is a schematic of a generic lead wire coated with crosslinked TPU.

A first embodiment of the invention will be described with reference to FIG. 1, FIG. 2, and FIG. 3. The cardiac pacemaker 20 contains at least one electrical contact 22 to which is attached an electrical lead wire 28. FIG. 2 depicts the electrical contact 22 composed of the electrically conductive element 26 insulated with the thermoset polyurethane coating 24. FIG. 3 depicts the electrical lead wire 28 composed of the electrically conductive wire 32 insulated with the thermoset polyurethane coating 24.

Once the thermoplastic polyurethane (TPU) has been extruded, molded, or otherwise applied onto the device or element, a process of crosslinking is performed to convert the TPU to a thermoset polyurethane. The TPU may contain a crosslinking agent such as an allylic monomer, acrylate, methacrylate, or combination thereof. The process of crosslinking involves bombarding the target device and TPU coating with radiation of a sufficient intensity and duration to affect the transformation of the TPU to a thermoset polyurethane. The dosage of radiation required for this transformation is preferably between 1 and 100 Mrads, more preferably between 10 and 20 Mrads, and most preferably approximately 15 Mrads. While both UV radiation and gamma radiation are suitable sources, the application of electron beam radiation forms the preferred method of radiation bombardment.

In addition, it is preferred that a crosslinking agent be incorporated into the TPU prior to the process of irradiation for the purpose of converting the TPU to a thermoset polyurethane. The crosslinking agent can be incorporated into, and preferably physically admixed with, the TPU either prior to or subsequent to the polymerization of the TPU.

TPU is suitably made by reacting an isocynate with a polyol. The TPU of choice for long term in vivo medical implantation is made from aliphatic isocyanate. However, aromatic TPU can be used. Preferred crosslinking agents include allylic monomers, although monomers containing acrylate or methacrylate moities, or other functional groups can be utilized as desired.

As used herein, the term "thermoplastic" is used in its broad sense to designate a material that is reprocessable at an elevated temperature, whereas "thermoset" designates a material that exhibits high temperature stability without such reprocessability at elevated temperatures. The term "crosslinked thermoplastic" designates a material that is reprocessible at an elevated temperature until it is crosslinked by some method after which it is without reprocessability at elevated temperatures. The term "thermoplastic elastomer" designates a material that possesses an elastic, rubber-like property such that it exhibits at least a one hundred percent elongation without breaking when stretched at room temperature, and will return to its unstretched length when released.

As used herein, the term "allylic monomer" is intended to designate a cross-linking moiety for polyurethanes that is monomeric and contains an allyl group. Preferably, the allylic monomer is free of peroxide, acrylate, and methacrylate moieties.

Particularly useful reactive monomers include, for example, triallylisocyanurate (also referred to herein as "TAIC"), triallylcyanurate (also referred to herein as "TAC"), diallylphthalate (also referred to herein as "DAP"), and meta-phenylene dimaleimide (also referred to herein as MPDM), and combinations thereof. The TAIC is commercially available as a liquid dispersion, and, alternatively, on a silicate substrate (75% TAIC on 25% silicate) as SYNPRO PLC-4185, a product of Synpron Corporation. Although less desired, other useful reactive monomers include methacrylate-containing monomers, such as trimethyolpropane trimethacrylate (TMPTMA), commercially available as Sartomer's SR-350.

The reactive monomer is suitably admixed with the polyurethane-forming composition prior to preparation of the TPU, or admixed with the TPU prior to preparation of the desired thermoset polyurethane product.

Although not wishing to be bound by any particular theory, it is believed that the essentially discoloration-free appearance of the thermoset polyurethanes produced in accordance with the present invention is attributable to the use of an aliphatic polyisocyanate in the polyurethane-forming compositions employed in the present invention. The present inventor has found that the irradiation employed in the present invention does not significantly discolor the aliphatic polyisocyanate-based polyurethane compositions employed in his invention. In contrast, such irradiation appears to severely discolor comparison polyurethane compositions based upon aromatic polyisocyanates. Further, the present inventor has found that aliphatic polyisocyanate-based TPUs are suitably converted to thermoset compositions by irradiation, whereas the benzene molecules in backbone on aromatic polyisocyanate-based TPU's seem to absorb high energy radiation (e-beam or gamma rays), thus rendering aromatic isocyanate-based TPU's stable (and, hence, not easily thermoset) in the presence of irradiation. Moreover, although aromatic polyisocyanate-based TPU's typically exhibit better chemical properties, such as resistance to organic solvents and oils, than prior art aliphatic polyisocyanate-based TPU, the compositions of the present invention overcome this disadvantage since the thermoset polyurethanes of the present invention exhibit excellent physical and chemical properties.

The aliphatic polyisocyanate useful as a reactant in forming the polyurethanes employed in the present invention is preferably selected from commercially-available aliphatic polyisocyanates such as, for example, 1,6-hexamethylene diisocyanate ("HDI"), isophorone diisocyanate ("IPDI"), ethylene diisocyanate, 1,4-tetramethylene diisocyanate, 2,2, 4-trimethyl-1,6-hexamethylene diisocyanate, 1,10-decanemethylene diisocyanate, 1,12-dodecanemethylene diisocyanate, cyclohexane-1,3-diisocyanate, cyclohexane-1, 4-diisocyanate, 1-isocyanato-2-isocyanatomethyl cyclopentane, isophorone diisocyanate, bis-(4-isocyanatocyclohexyl)-methane, 1,3- and/or 1,4-bis-(isocyanatomethyl)-cyclohexane, bis-(4-isocyanato-3-methylcyclohexyl)-methane, 1-isocyanato-1-methyl-4(3)-isocyanatomethyl cyclohexane, 4,4'-dicyclohexylmethane diisocyanate, and combinations thereof.

The "polyahl" useful as a reactant in forming the polyurethanes employed in the present invention is an active hydrogen-containing compound that is reactive with the aliphatic polyisocyanate to produce the desired polyurethane. In addition, the term polyahl is intended to encompass compounds that react in situ to generate an active hydrogen-containing moiety such as imines. An active hydrogen group is a group which has a hydrogen atom which, because of its position in the molecule, displays activity according to the Zerewitnoff test described by Woller in the Journal of American Chemical Society, Vol. 49, page 3181 (1927). Illustrative of such active hydrogen groups are —OH, —NH—, —COOH, —SH and —CONH—. Particularly suitably polyahis include polyols, imines (such as ketimines and aldimines), oxazolidines, and combinations thereof, preferably having a weight average molecular weight of between about 100 and about 10,000, more preferably between about 100 and about 5,000, most preferably between about 200 and about 2,000.

Suitable amines are aliphatic or cycloaliphatic, primary or secondary amines. Preferred amines are poly(alkyleneoxy) alkylamines.

Suitable polyols include polyether polyols and polyester polyols. The preferred polyols useful in the present invention have a hydroxyl functionality of no greater than about 2, more preferably less than 1.5, advantageously about 1, in order to prevent the formation of very high molecular weight polyurethane prepolymers which result in coating viscosities higher than desired for ready application. The polyether polyols are prepared by polymerization of alkylene oxides with water, polyhydric alcohols with two to eight hydroxyl groups, or amines. Polyester polyols are suitably prepared by a condensation reaction of a polycarboxylic acid with a polyhydric alcohol.

In preparing the polyurethanes useful in the present invention, the ratio of NCO equivalents in the polyisocyanate to the OH equivalents in the active hydrogen-containing compound can vary over a wide range of between about 10:1 and about 1:10, preferably between about 2:1 and about 1:2.

Catalysts are typically employed in the polyurethane-forming reaction. Useful catalysts include those which facilitate the reaction of the polyahl with the aliphatic polyisocyanate reactants. Suitable catalysts are the organotin catalysts, alone or in combination with amine catalysts, particularly tertiary amine catalysts. Illustrative organotin catalysts include dibutyltin dilaurate, stannous octoate, and combinations thereof. Illustrative amine catalysts include the following: N,N'-dimethylethanolamine, N,N-dimethylamino-ethoxyethanol, N,N'-dimethylaminoethyl-N-methylethanolamine, N,N-dimethyl-N',N'-2-hydroxypropyl-1,3-propylene diamine, N,N,N'-trimethyl-N'-hydroxyethyl-bis(amino ethyl) ether, N,N-bis(3-dimethylaminopropyl) amino-2-propanol, and combinations thereof. The catalysts are suitably employed in the polyurethane-forming formulation in a total amount of between about 0.01% and about 5%, preferably between about 0.01% and about 1%, by weight based upon the weight of the polyurethane-forming composition.

In preparing the desired polyurethane, the polyether polyol(s), polyisocyanate(s), chain extender(s) such as polyether or polyester glycol chain extenders, and other desired components, for example copolymers with other components such as silane are reacted, typically at an elevated temperature. One method of forming the desired thermoplastic polyurethane is by continuous processing utilizing an extruder, as illustrated by the disclosures of U.S. Pat. No. 3,642,964, incorporated herein by reference in its entirety. An alternative method involves batch processing, followed by grinding and extrusion of the formed elastomer as is well-known in the art. Although either the prepolymer method or the one-shot method can be used, the one-shot method is preferred. The one-shot method is intended to also include the process whereby the diisocyanate has been converted to a quasi-prepolymer by reaction with a minor amount (i.e., less than about 10 percent on an equivalent basis) of polyol prior to carrying out the polyurethane forming reaction.

In preparing the desired polyurethane, urethane forming catalysts can be used, as discussed above, as well as the usual compounding ingredients such as antioxidants or other antidegradants. Typical antioxidants include hindered phenols, butylated hydroxytoluene ("BHT"), and the like. Other optional compounding ingredients include, for example, plasticizers, adhesion promoters, flame retardants, fillers and pigments or dyes, such as clay, silica, fumed silica, carbon black, talc, phthalocyanine blue or green, $TiO_2$, U-V absorbers, $MgCO_3$, $CaCO_3$ and the like. The compounding ingredients are suitably employed in an amount of between 0 and about 75 weight percent based upon the weight of the elastomer.

The polymerization reaction may be carried out in a single reaction (one-shot process), or in one or more sequential steps (prepolymer process), using either bulk polymerization or solution polymerization. When solution polymerization is used, polar solvents such as tetrahydrofuran ("THF"), dimethylformamide ("DMF"), and dimethylacetamide ("DMAC") are typically utilized. In the one-shot process, all the isocyanate-reactive components are reacted simultaneously with the polyisocyanate. In such process, it is normal practice to blend all components except the polyisocyanate into a "B-side" mixture, which is then reacted with the polyisocyanate to form the polyurethane and/or polyurea elastomer. However, the order of mixing is not critical as long as the components do not undesirably react before all components are present. The reaction mixture is then suitably placed in a mold, or extruded through an extruder, and cured at a suitable temperature. The apparatus used for blending and molding is not especially critical. Hand mixing, conventional machine mixing, and the so-called reaction injection molding (RIM) equipment are all suitable. In the prepolymer process, all or a portion of one or more of the isocyanate reactive materials is reacted with a stoichiometric excess of the polyisocyanate to form an isocyanate-terminated prepolymer. This prepolymer is then allowed to react with the remaining isocyanate-reactive materials to prepare the polyurethane and/or polyurea elastomer. The prepolymer can be prepared with either the polyether or the chain extender, or a mixture of both.

The mixing of the reactants can be carried out at ambient temperature (typically from 20° C. to 25° C.) and the resulting mixture is then heated to a temperature of the order of about 40° C. to about 130° C., preferably to a temperature of about 90° C. to about 120° C. Alternatively, and preferably, one or more of the reactants is preheated to a temperature within the above ranges before the admixing is carried out. Advantageously, in a batch procedure, the heated reaction components are subjected to degassing in order to remove entrained bubbles of air, water, or other gases before the reaction takes place. This degassing is accomplished conveniently by reducing the pressure under which the components are maintained until no further evolution of bubbles occurs. The degassed reaction components are then admixed and transferred to suitable molds or extrusion equipment or the like and cured at a temperature of the order of about 20° C. to about 115° C. The time required for curing will vary the temperature of curing and also with the nature of the particular composition, as is known in the art.

Unless noted otherwise, wherever both English and metric units are given for a physical value, the English units shall be assumed to be the original measurement and the metric units a conversion therefrom.

What is claimed is:

1. A method for manufacturing a coated cardiac pacemaker or defibrillator lead or wire exhibiting enhanced in-vivo biostability, said method comprising:

(a) applying an insulating radiation cross-linkable thermoplastic polyurethane coating to the cardiac pacemaker or defibrillator lead or wire in order to insulate said lead or wire from in-vivo biological elements; and (b) irradiating said thermoplastic polyurethane coating with gamma or electron beam radiation at a dosage level sufficient to convert said thermoplastic polyurethane coating to a thermoset polyurethane coating, said dosage level being between 1 and 100 Mrads, said thermoset coating being electrically insulating, and exhibiting enhanced in-vivo biostability, relative to said thermoplastic coating, as evidenced by a reduction in a property selected from the group consisting of environmental stress cracking, metal ion oxidation and combinations thereof.

2. The method of claim 1 including the additional step of incorporating a crosslinking agent predominantly free of hydroxyl groups into the thermoplastic polyurethane coating prior to said irradiating of step (b).

3. The method of claim 2 wherein the crosslinking agent comprises an allylic monomer.

4. The method of claim 2 wherein the crosslinking agent comprises an acrylic or methacrylic monomer.

5. The method of claim 2 wherein the crosslinking agent comprises meta-phenylene dimaleimide.

6. The method of claim 1 wherein step(b) is effected simultaneously with, or after, step(a).

7. The method of claim 1 wherein the biomedical device comprises an electrically conductive wire.

8. The method of claim 1 wherein the polyurethane coating comprises an aromatic thermoplastic polyurethane.

9. The method of claim 1 wherein the polyurethane coating comprises an aliphatic thermoplastic polyurethane.

10. The method of claim 1 wherein the polyurethane coating comprises a mixture of differing amounts of aromatic and aliphatic polyurethanes.

11. The method of claim 1 wherein the polyurethane coating comprises differing amounts of thermoplastic polyurethane and other polymeric materials or a copolymer of TPU.

12. The method of claim 2 wherein said incorporating is effected by physically admixing said crosslinking agent with said thermoplastic coating.

* * * * *